United States Patent
Osawa (10) Patent No.: US 10,729,311 B2
(45) Date of Patent: Aug. 4, 2020

(54) SIGNAL PROCESSING SYSTEM AND ENDOSCOPE

(71) Applicant: OLYMPUS CORPORATION, Tokyo (JP)

(72) Inventor: Masato Osawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/445,373

(22) Filed: Jun. 19, 2019

(65) Prior Publication Data

US 2019/0298152 A1    Oct. 3, 2019

Related U.S. Application Data

(63) Continuation of application No. PCT/JP2018/017832, filed on May 8, 2018.

(30) Foreign Application Priority Data

Jul. 24, 2017  (JP) ................................ 2017-142886

(51) Int. Cl.
*A61B 1/00*     (2006.01)
*A61B 1/04*     (2006.01)
(Continued)

(52) U.S. Cl.
CPC .......... *A61B 1/00009* (2013.01); *A61B 1/00* (2013.01); *A61B 1/00006* (2013.01); *A61B 1/04* (2013.01);
(Continued)

(58) Field of Classification Search
CPC ................ A61B 1/00009; A61B 1/00006
See application file for complete search history.

(56) References Cited

U.S. PATENT DOCUMENTS 8,705,637 B2 *  4/2014  Shibata ............... H04L 25/0266
                                              327/108
9,191,591 B2 * 11/2015  Akahane .............. H04N 5/3575
(Continued)

FOREIGN PATENT DOCUMENTS

JP      2004-242878 A    9/2004
JP         5596888 B1    9/2014
(Continued)

OTHER PUBLICATIONS

International Search Report dated Jul. 31, 2018 issued in PCT/JP2018/017832.

*Primary Examiner* — Tuan H Nguyen
(74) *Attorney, Agent, or Firm* — Scully, Scott, Murphy & Presser, P.C.

(57) ABSTRACT

A signal processing system includes: a transmission channel; a common-mode signal transmitting circuit configured to output an uplink signal to the transmission channel in a common mode; a common-mode signal detecting circuit configured to detect a common-mode signal from the uplink signal transmitted by the transmission channel; a downlink reference clock signal generating circuit configured to generate a downlink reference clock signal at a second frequency with reference to the first clock edge of the common-mode signal detected by the common-mode signal detecting circuit; a downlink data generating circuit configured to generate downlink data; a differential signal transmitting circuit configured to output, as a downlink signal, the downlink data generated by the downlink data generating circuit to the transmission channel in a differential mode; and a differential signal receiving circuit configured to extract a differential signal from the downlink signal.

7 Claims, 7 Drawing Sheets

(51) Int. Cl.
    *H04N 5/376*      (2011.01)
    *H04N 5/378*      (2011.01)
    *H04N 7/18*       (2006.01)
    *G02B 23/24*      (2006.01)

(52) U.S. Cl.
    CPC ............ *H04N 5/376* (2013.01); *H04N 5/378*
        (2013.01); *H04N 7/18* (2013.01); *G02B 23/24*
                                                (2013.01)

(56) References Cited

U.S. PATENT DOCUMENTS

| | | |
|---|---|---|
| 9,813,645 B2 | 11/2017 | Ono et al. |
| 10,038,865 B2 | 7/2018 | Kagawa et al. |

FOREIGN PATENT DOCUMENTS

| | | |
|---|---|---|
| WO | WO 2014/115390 A1 | 7/2014 |
| WO | WO 2016/052173 A1 | 4/2016 |
| WO | WO 2016/104369 A1 | 6/2016 |
| WO | WO 2017/122626 A1 | 7/2017 |

\* cited by examiner

SIGNAL PROCESSING SYSTEM AND ENDOSCOPE

CROSS-REFERENCE TO RELATED APPLICATION

This application is a continuation of PCT International Application No. PCT/JP2018/017832, filed on May 8, 2018, which designates the United States, incorporated herein by reference, and which claims the benefit of priority from Japanese Patent Application No. 2017-142886, filed on Jul. 24, 2017, incorporated herein by reference.

BACKGROUND

1. Technical Field

The present disclosure relates to a signal processing system and an endoscope capable of performing bi-directional data communication via a transmission channel.

2. Related Art

In the related art, a technique of transmitting a plurality of signals from a processor to an endoscopy scope via a transmission cable in an endoscope system has been known (see Japanese Patent No. 5596888). In this technique, each of a power supply voltage, a ground, an imaging signal, a control signal, a reference clock signal, and a synchronous signal is transmitted between the processor and the endoscopy scope via the transmission cable.

SUMMARY

In some embodiments, a signal processing system includes: a transmission channel including at least a pair of signal lines; a common-mode signal transmitting circuit configured to output an uplink signal having a first clock edge that is repeated at a first frequency to the transmission channel in a common mode; a common-mode signal detecting circuit configured to detect a common-mode signal from the uplink signal transmitted by the transmission channel; a downlink reference clock signal generating circuit configured to generate a downlink reference clock signal at a second frequency with reference to the first clock edge of the common-mode signal detected by the common-mode signal detecting circuit; a downlink data generating circuit configured to generate downlink data based on the first clock edge of the common-mode signal detected by the common-mode signal detecting circuit; a differential signal transmitting circuit configured to output, as a downlink signal, the downlink data generated by the downlink data generating circuit to the transmission channel in a differential mode, based on the downlink reference clock signal generated by the downlink reference clock signal generating circuit; and a differential signal receiving circuit configured to receive the downlink signal transmitted by the transmission channel and extract a differential signal from the downlink signal.

In some embodiments, an endoscope includes: the signal processing system; an insertion portion to be inserted into a subject; and a connector removably connected to a control device that performs predetermined image processing. The insertion portion includes the common-mode signal detecting circuit, the downlink reference clock signal generating circuit, the downlink data generating circuit, and the differential signal transmitting circuit, and the connector includes the common-mode signal transmitting circuit and the differential signal receiving circuit.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, an endoscope system including a signal processing system in which a source device and a sink device are connected by a transmission channel will be described as modes (hereinafter, referred to as "embodiments") for carrying out the present disclosure. Further, the present disclosure is not limited by the embodiments. Furthermore, in descriptions of the drawings, the same or corresponding components are denoted by the same reference symbols. Moreover, it is necessary to note that the drawings are schematic, and a relation between a thickness and a width of each of components, ratios among the components, and the like are different from actual ones. In addition, the drawings may include a portion that has different dimensional relations or ratios.

First Embodiment

Configuration of Endoscope System

Figure 1:
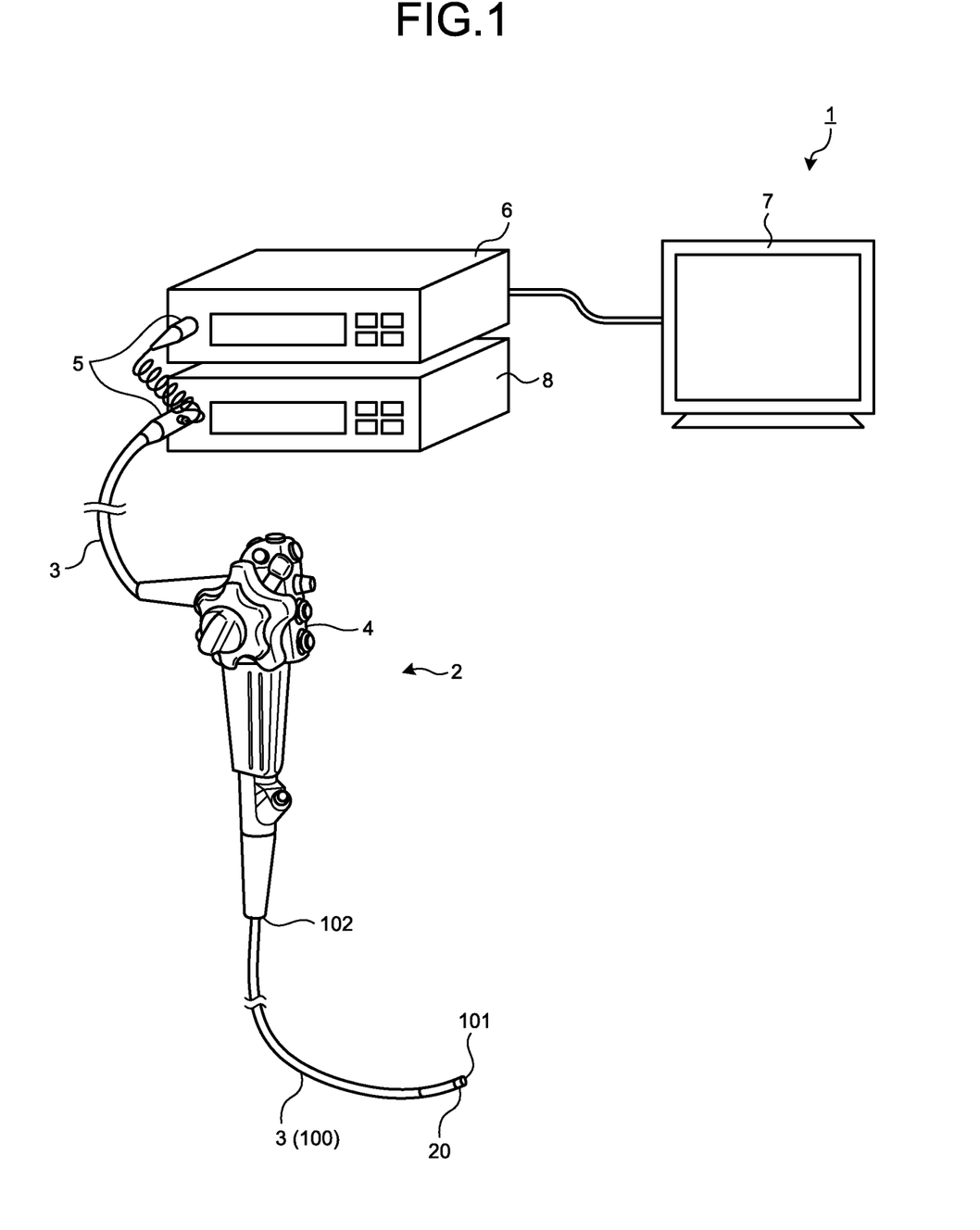
FIG. 1 is a schematic diagram schematically illustrating an entire configuration of an endoscope system according to a first embodiment of the present disclosure.

FIG. 1 is a schematic diagram schematically illustrating an entire configuration of an endoscope system according to a first embodiment of the present disclosure. An endoscope system 1 illustrated in FIG. 1 includes an endoscope 2 that functions as a source device, a transmission cable 3 that functions as a transmission channel, a connector 5 that functions as a sink device, a processor 6 (control device), a display device 7, and a light source device 8.

The endoscope 2 captures an image of the inside of a subject by inserting an insertion portion 100 that is a part of the transmission cable 3 into a body cavity of the subject, and outputs generated image data to the processor 6. Further, the endoscope 2 includes an imaging unit 20 that generates image data as downlink data, on a distal end portion 101 side of the insertion portion 100 that is to be inserted into the body cavity of the subject, i.e., on one end side of the transmission cable 3, and an operating unit 4 that receives various kinds of operation on the endoscope 2 is connected to a proximal end 102 side of the insertion portion 100. The image data generated by the imaging unit 20 is output to the connector 5 via the transmission cable 3 that has a length of at least 10 centimeters (cm) or longer.

The connector 5 is removably connected to each of the processor 6 and the light source device 8, performs predetermined signal processing on the image data output by the imaging unit 20, and outputs the image data to the processor 6.

The processor 6 performs predetermined image processing on an imaging signal input from the connector 5, and integrally connects the entire endoscope system 1.

The display device 7 displays an image corresponding to the image signal that is subjected to the image processing by the processor 6. Further, the display device 7 displays various kinds of information on the endoscope system 1.

The light source device 8 is configured using, for example, a halogen lamp or a white light emitting diode (LED), and emits illumination light toward the subject from the distal end portion 101 side of the insertion portion 100 of the endoscope 2 via the connector 5 and the transmission cable 3, under the control of the processor 6.

Functional Configuration of Main Components of Endoscope System

Figure 2:
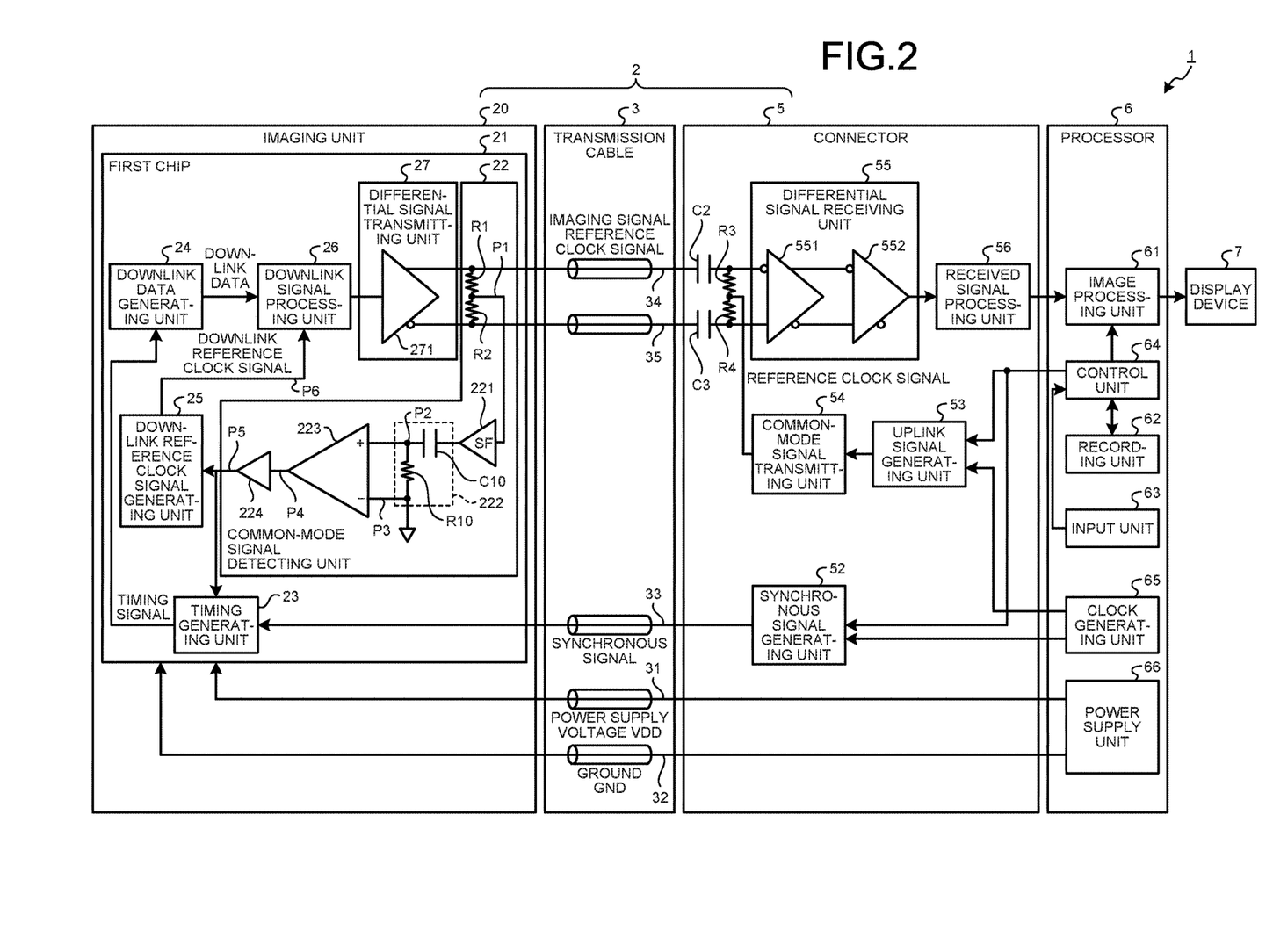
FIG. 2 is a block diagram illustrating a functional configuration of main components of the endoscope system according to the first embodiment of the present disclosure.
Figure 3:
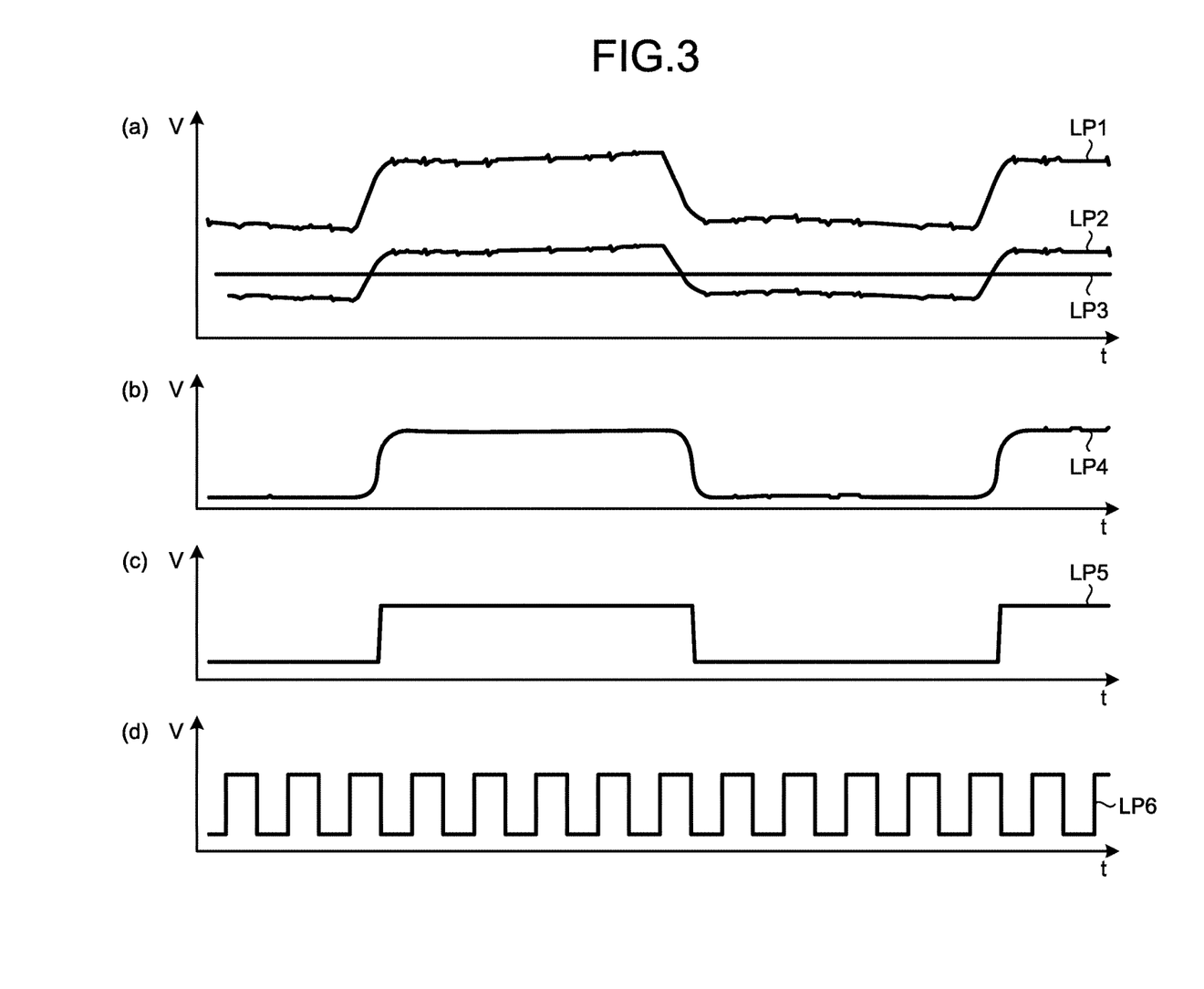
FIG. 3 is a diagram illustrating a signal waveform of each of nodes illustrated in FIG. 2.

Next, a functional configuration of main components of the endoscope system 1 as described above will be described. FIG. 2 is a block diagram illustrating the functional configuration of the main components of the endoscope system 1. FIG. 3 is a diagram illustrating a signal waveform of each of nodes P1 to P6 illustrated in FIG. 2. In FIG. 3, a curve LP1 in (a) of FIG. 3 represents the signal waveform of the node P1, a curve LP2 in (a) of FIG. 3 represents the signal waveform of the node P2, a straight line LP3 in (a) of FIG. 3 represents the signal waveform of the node P3, a curve LP4 in (b) of FIG. 3 represents the signal waveform of the node P4, a curve LP5 in (c) of FIG. 3 represents the signal waveform of the node P5, and a broken line LP6 in (d) of FIG. 3 represents the signal waveform of the node P6. Further, in FIG. 3, the horizontal axis represents a time (t) and the vertical axis represents a voltage (v).

Configuration of Endoscope

First, the endoscope 2 will be described.

As illustrated in FIG. 2, the endoscope 2 includes the imaging unit 20, the transmission cable 3, and the connector 5.

As illustrated in FIG. 2, the imaging unit 20 includes at least a first chip 21. The first chip 21 is a single-layer or multi-layer semiconductor substrate with a size smaller than 1 cm×1 cm in a horizontal direction along which a plurality of functional elements (to be described later) are arranged. Further, the imaging unit 20 receives, via the transmission cable 3, electrical signals of a power supply voltage VDD and a ground GND generated by a power supply unit 66 in the processor 6.

The first chip 21 includes a common-mode signal detecting unit 22, a timing generating unit 23, a downlink data generating unit 24, a downlink reference clock signal generating unit 25, a downlink signal processing unit 26, and a differential signal transmitting unit 27.

The common-mode signal detecting unit 22 detects a reference clock signal that is a common-mode signal from an uplink signal that is transmitted in a common mode (common mode signal) from the connector 5 via the transmission cable 3 and that has a first clock edge repeated at a first frequency. The common-mode signal detecting unit 22 includes resistors R1 and R2, a buffer circuit 221 (source follower circuit: SF circuit), a high-pass filter circuit 222, a comparator 223, and a buffer circuit 224. The resistor R1 and the resistor R2 have the same resistance values. The buffer circuit 221 is a circuit that buffers and outputs a signal VOUTCOM (the curve LP1 in FIG. 3) of an intermediate voltage of the resistors R1 and R2, and prevents the signal VOUTCOM from being distorted due to the influence of input capacitance of the high-pass filter circuit 222 in the subsequent stage. The high-pass filter circuit 222 is configured using an RC circuit including a capacitor C10 and a resistor R10, and outputs a signal VOUTCOM_HP (the curve LP2 in FIG. 3) that is obtained by attenuating components at frequencies lower than a cutoff frequency with respect to a signal that is amplified by the buffer circuit 221. The comparator 223 generates a pre-reference clock signal PRE_BASE_CLK (the curve LP4 in FIG. 3) by comparing magnitudes of a voltage of the signal VOUTCOM_HP that is input from the high-pass filter circuit 222 to a first terminal and a voltage of a reference voltage VREF (the straight line LP3 in FIG. 3), and outputs the pre-reference clock signal PRE_BASE_CLK. The buffer circuit 224 amplifies a reference clock signal BASE_CLK input from the comparator 223, and outputs the reference clock signal BASE_CLK (the curve LP5 in FIG. 3) to each of the timing generating unit 23 and the downlink reference clock signal generating unit 25.

The timing generating unit 23 generates a timing signal for driving the downlink data generating unit 24 on the basis of a synchronous signal input from the connector 5 via the transmission cable 3 and the reference clock signal BASE_CLK input from the common-mode signal detecting unit 22, and outputs the timing signal to the downlink data generating unit 24. The timing generating unit 23 is configured using a timing generator or the like.

The downlink data generating unit 24 generates downlink data to be transmitted to the processor 6 via the transmission cable 3 and the connector 5 on the basis of the timing signal input from the timing generating unit 23, and outputs the downlink data to the downlink signal processing unit 26. The downlink data generating unit 24 includes an imaging element, such as a charge coupled device (CCD) image sensor or a complementary metal oxide semiconductor (CMOS) image sensor, that generates image data by performing photoelectric conversion on incident light, or at least one or more of a physical sensor that detects a physical quantity. Here, at least one or more of the following physical sensors and chemical sensors are used as the physical sensor: a detection sensor, such as an acceleration sensor or a gyroscope sensor, that generates movement data for detecting movement of the imaging unit 20, a temperature sensor, such as a thermistor, that detects temperature of the imaging unit 20 and generates temperature data, a pressure sensor that detects pressure and generates pressure data, a humidity sensor that detects humidity and generates humidity data, a magnetic sensor that detects magnetism and generates magnetic data, a pH sensor that detects an ion concentration of hydrogen ion and detects hydrogen ion index data, and a radiation sensor that detects a radiation dose and generates radiation data. In the first embodiment, the imaging element is described as a CMOS image sensor that is a circuit block in which photodiodes for outputting electrical signals corresponding to incident light are two-dimensionally arranged in the horizontal and the vertical directions in a semiconductor substrate surface; however, an imaging element of other embodiments may be a line sensor in which photodiodes are arranged only in the horizontal direction in the semiconductor substrate surface. Meanwhile, the downlink data generating unit 24 includes an analog signal processing circuit that performs predetermined signal processing including, for example, an amplification process or filtering, on an analog signal output from a physical sensor or a chemical sensor as needed. In the first embodiment, the downlink data generating unit 24 outputs downlink data that is converted to a digital signal by an analog-to-digital (A/D) conversion processing circuit implemented in the downlink data generating unit 24. In other words, the downlink data generating unit 24 generates, as the downlink data, digital data representing image data and outputs the digital data to the downlink signal processing unit 26. Meanwhile, in the first embodiment, it is assumed that a pixel rate of the imaging element is 10 Mpixel/sec and the A/D conversion processing circuit outputs 10-bit width data.

The downlink reference clock signal generating unit 25 generates a downlink reference clock signal that is a clock signal at a second frequency with reference to the first clock edge of the reference clock signal BASE_CLK being a common-mode signal input from the common-mode signal detecting unit 22 and that serves as a downlink reference signal when the differential signal transmitting unit 27 transmits a downlink signal, and outputs the downlink reference clock signal to the downlink signal processing unit 26 (the broken line LP6 in FIG. 3). The downlink reference clock signal generating unit 25 is configured using a phase locked loop (PLL) circuit or the like, multiplies a frequency of the reference clock signal BASE_CLK, which is input from the common-mode signal detecting unit 22 and which has the first clock edge at the first frequency, to obtain the second frequency, and outputs the reference clock signal to the downlink signal processing unit 26. Specifically, the downlink reference clock signal generating unit 25 multiplies the reference clock signal (for example, a clock signal at 10 MHz: hereinafter, denoted by "10MCLK") input from the common-mode signal detecting unit 22 by a factor of 1 or more, in particular, by a factor of 10 (for example, a clock signal at 100 MHz: hereinafter, denoted by "100MCLK"), and outputs the reference clock signal to the downlink signal processing unit 26.

The downlink signal processing unit 26 performs parallel-to-serial conversion on the image data input from the downlink data generating unit 24, and outputs the image data to the differential signal transmitting unit 27 at a timing synchronized with the downlink reference clock signal that is generated by the downlink reference clock signal generating unit 25. The image data in the first embodiment is 10-bit width data with 10 Mpixel/sec, so that the image data synchronized with 100MCLK is output as serial data to the differential signal transmitting unit 27. The downlink signal processing unit 26 may add redundant bit information for error correction or may perform an encoding process, such as Manchester coding or Turbo coding, as needed, in addition to the parallel-to-serial conversion.

The differential signal transmitting unit 27 transmits the downlink data input from the downlink signal processing unit 26 to the connector 5 in a differential mode via two transmission lines 34 and 35 in the transmission cable 3. The differential signal transmitting unit 27 includes at least a differential signal transmission amplification unit 271 (low voltage differential signaling (LVDS)).

Configuration of Transmission Cable

Next, a configuration of the transmission cable 3 will be described.

The transmission cable 3 is configured using, for example, a coaxial cable or the like, and includes a transmission line 31 (power supply line) for transmitting the power supply voltage VDD, a ground line 32, a transmission line 33 for transmitting a synchronous signal, and the transmission lines 34 and 35 as a pair for transmitting a differential signal. The transmission cable 3 has a length of, for example, 10 cm or longer, and connects the imaging unit 20 and the connector 5.

Configuration of Connector

Next, a configuration of the connector 5 will be described.

The connector 5 includes capacitors C2 and C3, resistors R3 and R4, a synchronous signal generating unit 52, an uplink signal generating unit 53, a common-mode signal transmitting unit 54, a differential signal receiving unit 55, and a received signal processing unit 56.

The capacitors C2 and C3 are respectively provided on the transmission lines 34 and 35 and remove direct-current components contained in the transmission lines 34 and 35.

To match characteristic impedances of the transmission lines 34 and 35, the resistors R3 and R4 are provided at respective terminal ends of the transmission lines 34 and 35. The resistors R3 and R4 have the same resistance values.

The synchronous signal generating unit 52 generates a synchronous signal representing a start position of each frame, on the basis of a reference clock signal used as a reference of operation of each of the components of the endoscope 2 and a control command, which are supplied from a control unit 64 and a clock generating unit 65 of the processor 6, and outputs the synchronous signal to the timing generating unit 23 via the transmission cable 3. Here, the synchronous signal generated by the synchronous signal generating unit 52 includes a horizontal synchronous signal and a vertical synchronous signal.

The uplink signal generating unit 53 generates a reference clock signal that has the first clock edge repeated at the first frequency, on the basis of a clock signal supplied from the control unit 64 and the clock generating unit 65 of the processor 6, and outputs the reference clock signal to the common-mode signal transmitting unit 54.

The common-mode signal transmitting unit 54 outputs an uplink signal including the reference clock signal that is input from the uplink signal generating unit 53 and that has the first clock edge repeated at the first frequency (for example, 10MCLK) to the transmission cable 3 in a common mode, to thereby transmit the reference clock signal to the imaging unit 20.

The differential signal receiving unit 55 receives a differential signal including a common-mode signal that is transmitted in a differential mode via the transmission cable 3, and extracts only digital information included in the differential signal. The differential signal receiving unit 55 includes a differential amplifier 551 that extracts only a component of a differential signal from the differential signal including the common-mode signal that is transmitted via the transmission cable 3, and a differential single-ended converter 552 that shapes the differential signal output from the differential amplifier 551, converts the differential signal to a digital signal, and outputs the digital signal.

The received signal processing unit 56 performs predetermined processing on the signal input from the differential signal receiving unit 55, and outputs the signal to an image processing unit 61 of the processor 6.

Configuration of Processor

Next, a configuration of the processor 6 will be described.

The processor 6 is a control device that integrally controls the entire endoscope system 1. The processor 6 includes the image processing unit 61, a recording unit 62, an input unit 63, the control unit 64, the clock generating unit 65, and the power supply unit 66.

The image processing unit 61 converts a digital imaging signal that has been subjected to signal processing by the received signal processing unit 56 to an image signal by performing image processing, such as a synchronization process, a white balance (WB) adjustment process, a gain adjustment process, a γ correction process, a digital-to-analog (D/A) conversion process, and a format conversion process, on the digital imaging signal, and outputs the image signal to the display device 7, under the control of the control unit 64.

The recording unit 62 records therein various programs executed by the endoscope system 1, data being processed, image data, and the like. The recording unit 62 is configured using a volatile memory or a non-volatile memory.

The input unit 63 receives input of various kinds of operation on the endoscope system 1. For example, the input unit 63 receives input of an instruction signal for changing a type of illumination light emitted by the light source device 8 and an instruction signal for designating termination. The input unit 63 is configured using, for example, a cross switch, a push button, a touch panel, or the like.

The control unit 64 integrally controls each of the units included in the endoscope system 1. The control unit 64 is configured using a central processing unit (CPU) or the like. The control unit 64 changes illumination light emitted by the light source device 8 in accordance with an instruction signal input from the input unit 63.

The clock generating unit 65 generates a reference clock signal that is used as a reference of operation of each of the components of the endoscope system 1, and outputs the reference clock signal to the synchronous signal generating unit 52 and the uplink signal generating unit 53.

The power supply unit 66 generates the power supply voltage VDD, and supplies the generated power supply voltage VDD together with the ground GND to the imaging unit 20.

Configuration of Display Device

Next, a configuration of the display device 7 will be described.

The display device 7 displays an image captured by the imaging unit 20, on the basis of an image signal input from the image processing unit 61. The display device 7 is configured using a display panel made of liquid crystal, organic electro luminescence (EL), or the like.

Signal Waveform on Each Transmission Channel

Figure 4:
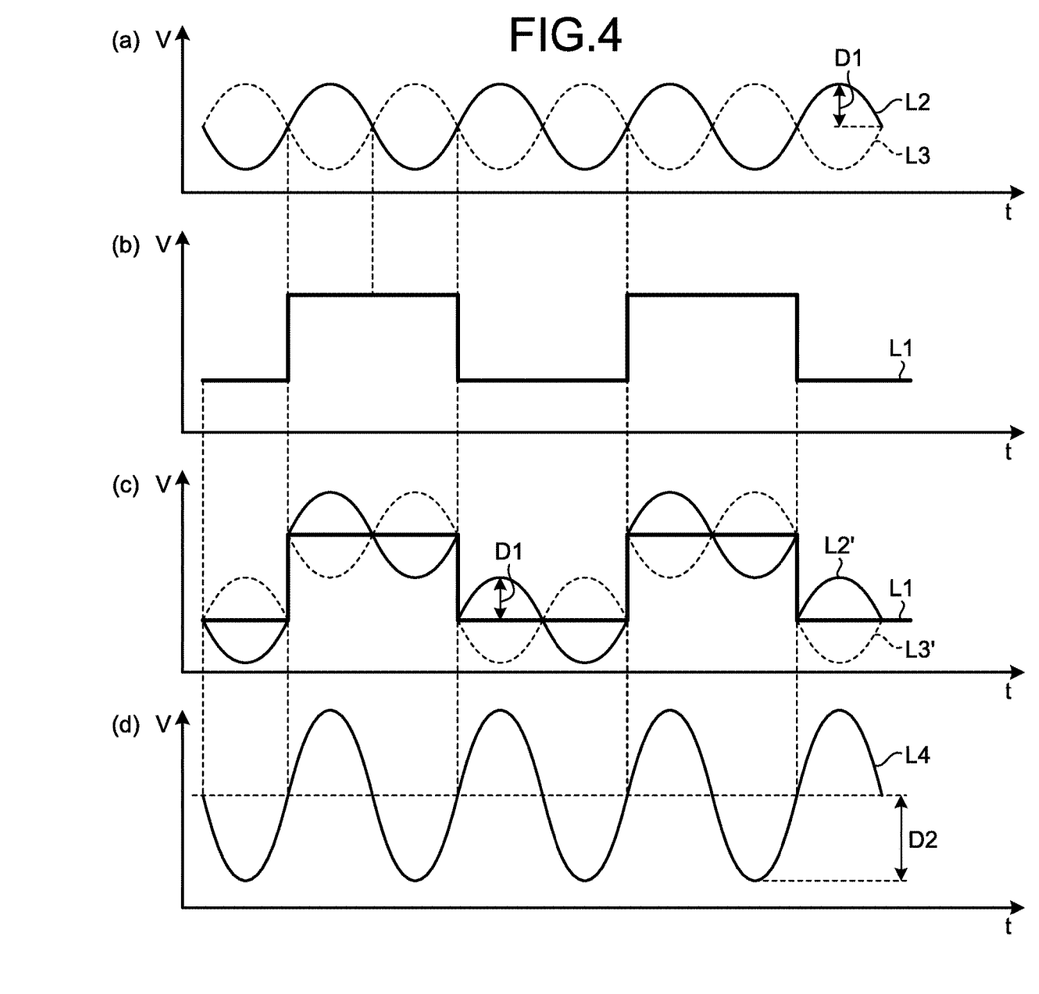
FIG. 4 is a diagram schematically illustrating a signal waveform on each of transmission channels in FIG. 2.

Next, a signal waveform on each of the transmission channels in FIG. 2 will be described. FIG. 4 is a diagram schematically illustrating the signal waveform on each of the transmission channels in FIG. 2. In FIG. 4, (a) of FIG. 4 illustrates a signal waveform of a differential signal transmitted by the differential signal transmitting unit 27, (b) of FIG. 4 illustrates a signal waveform of a reference clock signal transmitted by the common-mode signal transmitting unit 54, (c) of FIG. 4 illustrates signal waveforms that are actually transmitted on the transmission lines 34 and 35 in FIG. 2, and (d) of FIG. 4 illustrates a difference signal waveform of a differential signal transmitted by the differential signal transmitting unit 27. Further, in (a) to (d) of FIG. 4, the horizontal axis represents a time (t) and the vertical axis represents a voltage (v). Furthermore, curves L2 and L3 in (a) of FIG. 4 represent waveforms of differential signals transmitted by the transmission lines 34 and 35 in FIG. 2, a broken line L1 illustrated in (b) of FIG. 4 represents a signal waveform of the reference clock signal transmitted by the common-mode signal transmitting unit 54, and curves L2' and L3' in (c) of FIG. 4 indicate the differential signals that are actually transmitted on the transmission lines 34 and 35 in FIG. 2. The curves L2' and L3' have waveforms in which the curve L2 and the curve L3 are superimposed on the broken line L1. A curve L4 in (d) of FIG. 4 represents a difference signal waveform of a differential signal represented by a difference between the curves L2' and L3', and this difference signal waveform is the same as a difference signal waveform of a differential signal represented by a difference between the curve L2 and the curve L3. As indicated by the curves L2, L3, L2', L3', and L4, an amplitude D2 of the difference signal waveform of the differential signal transmitted by the differential signal transmitting unit 27 is twice an amplitude D1 of the curves L2' and L3' that are signals that appear on the transmission lines 34 and 35 in FIG. 2.

As illustrated in (c) of FIG. 4, the common-mode signal transmitting unit 54 transmits the signal VOUTCOM of the intermediate voltage of the resistors R1 and R2 to the transmission lines 34 and 35 in the common mode. Therefore, it is possible to simultaneously transmit the reference clock signal that is a common-mode signal such that the reference clock signal is superimposed on a differential-mode signal that is output by the differential signal transmitting unit 27 to the pair of the transmission lines 34 and 35.

According to the first embodiment of the present disclosure as described above, it is possible to reduce the three lines that are conventionally needed for the reference signals of the pair of the transmission lines 34 and 35 and the clock signal to two lines, so that it is possible to reduce a diameter of the transmission cable 3.

Further, according to the first embodiment of the present disclosure, the common-mode signal transmitting unit 54 outputs the uplink signal that has the first clock edge repeated at the first frequency to the transmission lines 34 and 35 in the common mode, and at the same time, the differential signal transmitting unit 27 outputs the imaging signal to the transmission lines 34 and 35 in the differential mode, so that it is possible to realize full-duplex transmission. Due to the full-duplex transmission, the downlink reference clock signal at the second frequency generated by the downlink reference clock signal generating unit 25 is generated based on the repetition frequency of the first clock edge of the uplink signal that is continuously supplied, so that is is possible to generate the downlink reference clock signal with high frequency accuracy.

Furthermore, according to the first embodiment of the present disclosure, the common-mode signal detecting unit 22 detects the uplink signal that is transmitted in the common mode and that has the first clock edge repeated at the first frequency, the downlink reference clock signal generating unit 25 generates the downlink reference clock signal at the second frequency that is higher than the first frequency, and the differential signal transmitting unit 27 transmits a video signal (image data) at the second frequency to the transmission cable 3 in a differential mode. In general, when a diameter of a cable is constant, it is possible to transmit signals at higher speed in differential mode transmission than in common mode (single ended) transmission. Therefore, according to the first embodiment of the present disclosure, by allocating the uplink signal that transitions at the first frequency corresponding to a relatively low speed to the common mode and allocating the downlink signal (video signal) that transitions at the second frequency corresponding to a relatively high speed to the differential mode, it is possible to transmit signals even by using the transmission cable 3 having the reduced diameter.

Moreover, according to the first embodiment of the present disclosure, by aggregating the cable lines, it is possible to reduce the number of bonding pads that are needed to connect the first chip 21 and the transmission cable 3 by one. The common-mode signal detecting unit 22 is realized by a simple configuration including the buffer circuit 221, the high-pass filter circuit 222, the comparator 223, and the buffer circuit 224, and therefore, it is possible to reduce a chip area needed to realize these circuit blocks relative to an area that is needed for a general bonding pad. As a result, it is possible to reduce the area of the first chip 21.

Second Embodiment

Next, a second embodiment of the present disclosure will be described. An endoscope system according to the second embodiment has a different configuration from the endoscope system 1 according to the first embodiment as described above. Specifically, the endoscope system 1 according to the first embodiment described above independently transmit the synchronous signal to the first chip 21, but the endoscope system according to the second embodiment transmits the reference clock signal and the synchronous signal in the common mode in a superimposed manner. In the following, the configuration of the endoscope system according to the second embodiment will be described. Meanwhile, the same components as those of the endoscope system 1 according to the first embodiment as described above are denoted by the same reference symbols, and explanation thereof will be omitted.

Functional Configuration of Main Components of Endoscope System

Figure 5:
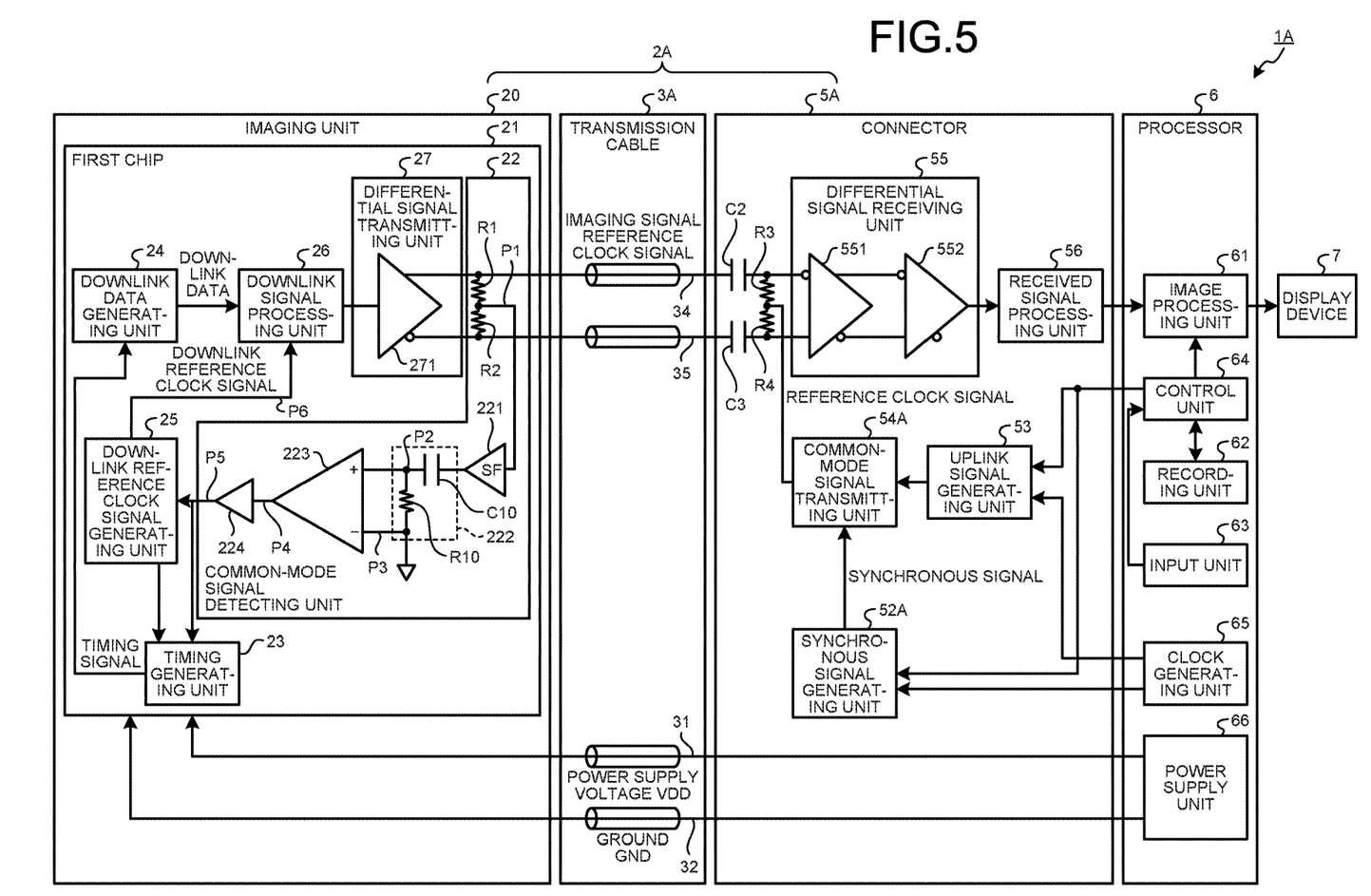
FIG. 5 is a block diagram illustrating a functional configuration of main components of an endoscope system according to a second embodiment of the present disclosure.

FIG. 5 is a block diagram illustrating a functional configuration of main components of the endoscope system according to the second embodiment of the present disclosure. An endoscope system 1A illustrated in FIG. 5 includes an endoscope 2A instead of the endoscope 2 of the endoscope system 1 according to the first embodiment described above.

Configuration of Endoscope

The endoscope 2A illustrated in FIG. 5 includes a transmission cable 3A and a connector 5A instead of the transmission cable 3 and the connector 5 according to the first embodiment described above.

Configuration of Transmission Cable

First, a configuration of the transmission cable 3A will be described.

The transmission cable 3A is configured using, for example, a coaxial cable or the like, and includes the transmission line 31 for transmitting the power supply voltage VDD, the ground line 32, and the two transmission lines 34 and 35 for transmitting differential signals.

Configuration of Connector

Next, a configuration of the connector 5A will be described.

The connector 5A illustrated in FIG. 5 includes a synchronous signal generating unit 52A and a common-mode signal transmitting unit 54A instead of the synchronous signal generating unit 52 and the common-mode signal transmitting unit 54 of the connector 5 according to the first embodiment described above.

The synchronous signal generating unit 52A generates a synchronous signal representing a start position of each frame, on the basis of a reference clock signal used as a reference of operation of each of the components of the endoscope 2A and a control command, which are supplied from the control unit 64 and the clock generating unit 65 of the processor 6, and outputs the synchronous signal to the common-mode signal transmitting unit 54A.

The common-mode signal transmitting unit 54A outputs an uplink signal including the reference clock signal that is input from the uplink signal generating unit 53 and the synchronous signal that is input from the synchronous signal generating unit 52A to the transmission cable 3A in the common mode, to thereby transmit the reference clock signal and the synchronous signal to the imaging unit 20. Specifically, the common-mode signal transmitting unit 54A outputs at least one of a pulse-width-modulated signal that is obtained by modulating a pulse width of the uplink signal and an amplitude-modulated signal that is obtained by modulating an amplitude of the uplink signal to the transmission cable 3A. For example, the common-mode signal transmitting unit 54A generates the pulse-width-modulated signal in which the pulse width is modulated by superimposing the synchronous signal on the reference clock signal, and outputs the pulse-width-modulated signal to the transmission cable 3A.

Signal Waveforms Detected by Common-Mode Signal Detecting Unit

Figure 6:
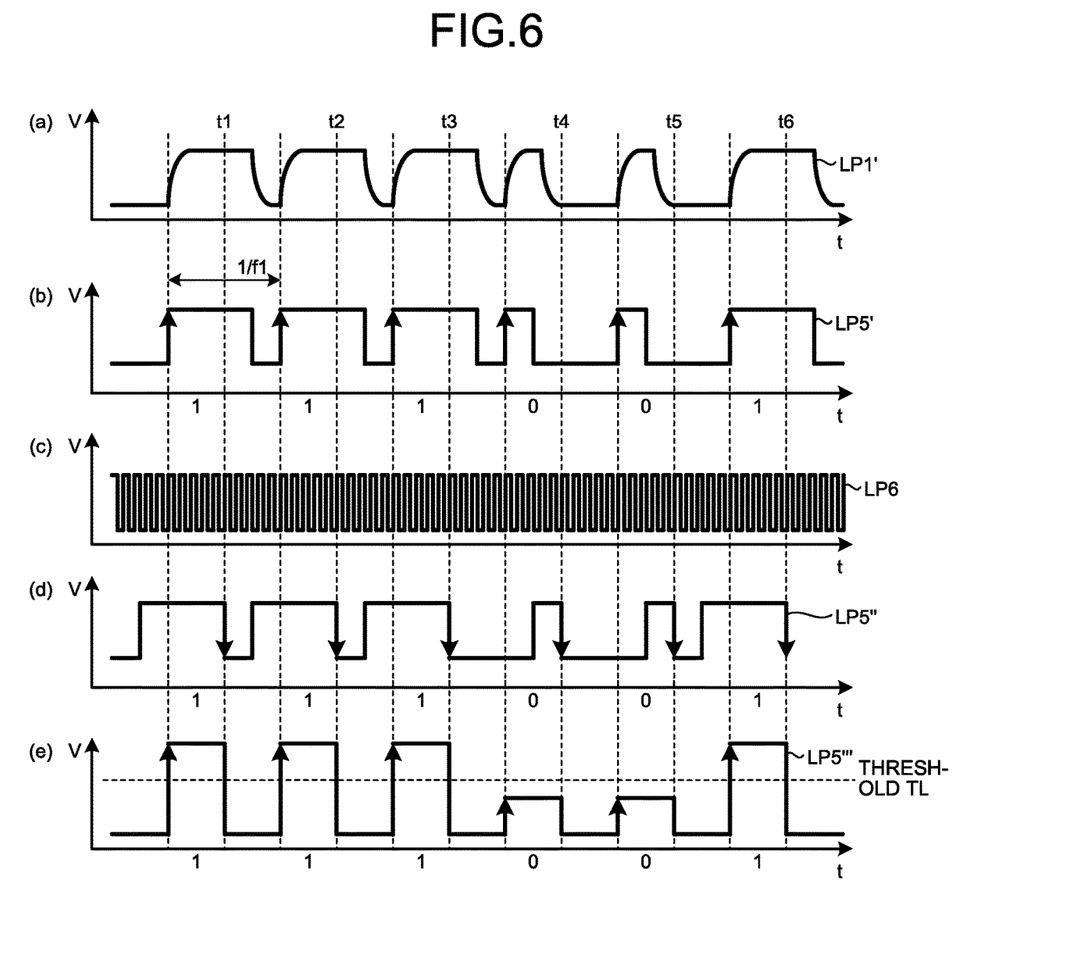
FIG. 6 is a diagram schematically illustrating signal waveforms that are detected by a common-mode signal detecting unit included in the endoscope system according to the second embodiment of the present disclosure.

Next, signal waveforms detected by the common-mode signal detecting unit 22 in FIG. 5 will be described. FIG. 6 is a diagram schematically illustrating the signal waveforms detected by the common-mode signal detecting unit 22. In FIG. 6, a curve LP1' in (a) of FIG. 6 represents a pulse-width-modulated reference clock signal (a signal corresponding to LP1 in FIG. 3) input to the common-mode signal detecting unit 22, a broken line LP5' in (b) of FIG. 6 represents a downlink reference clock signal (a signal corresponding to LP5 in FIG. 3) extracted and shaped by the common-mode signal detecting unit 22, and a broken line LP6 in (c) of FIG. 6 represents a downlink reference clock signal generated by the downlink reference clock signal generating unit 25 (a position of the first clock edge is the same as in FIG. 3 described above, and therefore, LP6 in FIG. 3 and LP6 in FIG. 6 are the same signals). Further, in (a), (b), (c), (d), and (e) of FIG. 6, the horizontal axis represents a time (t) and the vertical axis represents a voltage (V). Furthermore, in FIG. 6, the principle that each of the waveforms appears and is extracted is the same as described above with reference to FIG. 3, and therefore, detailed explanation thereof will be omitted.

As illustrated in FIG. 6, the downlink reference clock signal generating unit 25 outputs the downlink reference clock signal to each of the downlink signal processing unit 26 and the timing generating unit 23. The timing generating unit 23 extracts a synchronous signal from a pulse-width-modulated signal that is an uplink signal, on the basis of the broken line LP5' representing the reference clock signal input from the common-mode signal detecting unit 22 and the broken line LP6 representing the downlink reference clock signal input from the downlink reference clock signal generating unit 25. For example, as indicated in a portion below the broken line LP5' in (b) of FIG. 6, the timing generating unit 23 detects the synchronous signal depending on whether the broken line LP5' representing the reference clock signal is "1 (High)" or "0 (Lo)" at a timing of a rising edge of a sixth clock of the downlink reference clock signal represented by the broken line LP6 in (c) of FIG. 6 (times t1 to t6 in FIG. 6) by using each of the first clock edges (rising edges in this example) of the reference clock signal represented by the broken line LP5' as a reference point. In the example in FIG. 6, "1", "1", "1", "0", "0", and "1" are detected as a synchronous signal, and a timing control signal based on a detection result is output to the downlink data generating unit 24. Therefore, it is possible to omit a transmission line for transmitting a synchronous signal, so that it is possible to reduce a diameter of the transmission cable 3A.

In the example illustrated in FIG. 6, the pulse-width-modulated signal in the reference clock signal and the synchronous signal transmitted to the imaging unit 20 corresponds to the synchronous signal, and when a data string of the pulse-width-modulated signal has a data pattern of "1", "1", "1", "0", "0", "1", the pulse-width-modulated signal corresponds to a horizontal synchronous signal for starting to read a horizontal line. Therefore, when the data string of the pulse-width-modulated signal has the data pattern of "1", "1", "1", "0", "0", "1", the timing generating unit 23 determines that the pulse-width-modulated signal is a horizontal synchronous signal for starting to read a horizontal line, and starts to read in the horizontal direction (line direction). Further, when the data string of the pulse-width-modulated signal has a data pattern of "1", "0", "1", "0", "1", "1", the pulse-width-modulated signal corresponds to a vertical synchronous signal for starting to read a video frame. Therefore, when the data string of the pulse-width-modulated signal has the data pattern of "1", "0", "1", "0", "1", "1", the timing generating unit 23 determines that the pulse-width-modulated signal is a vertical synchronous signal for starting to read a video frame, and starts to read in the vertical direction (read one video frame). Furthermore, the common-mode signal transmitting unit 54A continuously output a signal by which the data string of the pulse-width-modulated signal becomes "0" during a period in which the synchronous signal generating unit 52A does not output the synchronous signal.

Meanwhile, the synchronous signal may have an arbitrary data string as long as the timing generating unit 23 is able to determine start in the horizontal line or start of a video frame. For example, a synchronous signal indicating a start in the horizontal line may have a data string of "0", "1", "0", "1", and a synchronous signal indicating start of read of a video frame may have a data string of "0", "0", "1", "1". Furthermore, the common-mode signal transmitting unit 54A may continuously output a signal by which the data string of the pulse-width-modulated signal becomes "1" during a period in which the synchronous signal generating unit 52A does not output the synchronous signal.

Meanwhile, the waveform of the curve LP1' represents a pulse-width-modulated signal which has a rising edge as the first clock edge with the constant first frequency f1 as the repetition frequency and for which the length of a pulse width is determined depending on whether a position of a falling clock edge is before or after a position of a rising edge of the sixth clock of the downlink reference clock represented by the broken line LP6. Therefore, as illustrated in the broken line LP5" in (d) of FIG. 6, it may be possible to adopt a pulse-width-modulated signal for which a falling edge serves as the first clock edge, a repetition frequency is the constant first frequency f1, and the length of a pulse width is determined depending on whether a position of a rising clock edge is before or after a position of a rising edge of the clock at each of the times t1 to t6 in FIG. 6.

Furthermore, as illustrated in a broken line LP5''' in (e) of FIG. 6, it may be possible to adopt a pulse-width-modulated signal for which a rising edge serves as the first clock edge, a repetition frequency is the constant first frequency f1, and a size of a pulse voltage is determined depending on whether a voltage of a rising clock edge is equal to or larger than a threshold TL or smaller than the threshold TL.

According to the second embodiment of the present disclosure as described above, by outputting at least one of the pulse-width-modulated signal obtained by modulating the pulse width of the uplink signal by the common-mode signal transmitting unit 54 and an amplitude modulated signal obtained by modulating the amplitude of the uplink signal to the transmission cable 3A, and by superimposing the synchronous signal on the reference clock signal, it is possible to reduce the number of transmission lines in the transmission cable 3A to four, so that it is possible to reduce the diameter of the transmission cable 3A.

Meanwhile, in the second embodiment of the present disclosure, the common-mode signal transmitting unit 54A outputs the pulse-width-modulated signal obtained by modulating the pulse width of the uplink signal to the transmission cable 3A, but embodiments are not limited thereto. It may be possible to output an amplitude modulated signal obtained by modulating the amplitude of the uplink signal to the transmission cable 3A, or output a modulated signal obtained by modulating both of the pulse width and the amplitude of the uplink signal to the transmission cable 3A.

Third Embodiment

Next, a third embodiment of the present disclosure will be described. An endoscope system according to the third embodiment has a different configuration from the endoscope system 1 according to the first embodiment described above. Specifically, the endoscope system according to the third embodiment includes a common-mode signal detecting unit having a different configuration. In the following, the configuration of the endoscope system according to the third embodiment will be described. Meanwhile, the same components as those of the endoscope system 1 according to the first embodiment as described above are denoted by the same reference symbols, and explanation thereof will be omitted.

Functional Configuration of Main Components of Endoscope System

Figure 7:
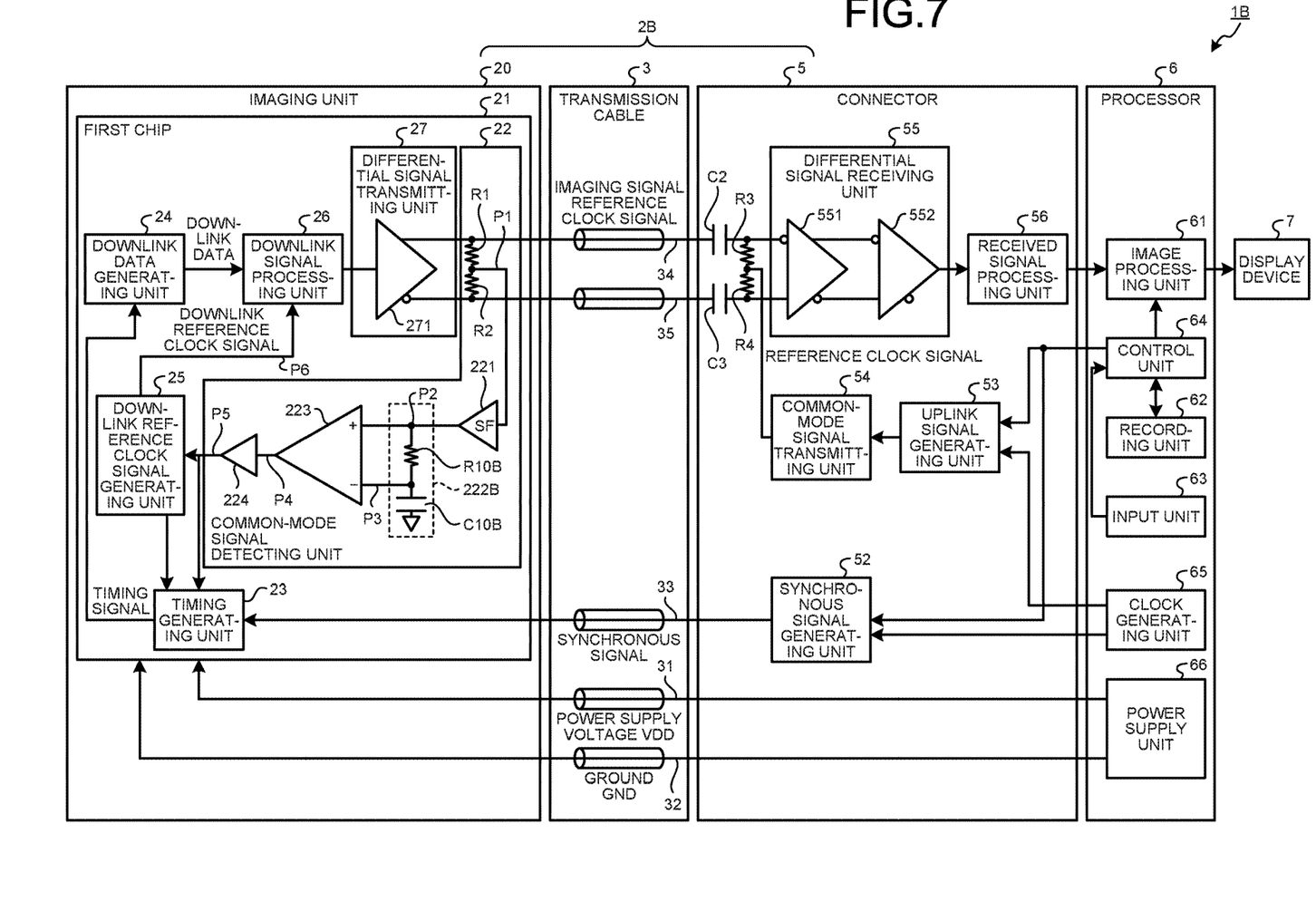
FIG. 7 is a block diagram illustrating a functional configuration of main components of an endoscope system according to a third embodiment of the present disclosure.

FIG. 7 is a block diagram illustrating a functional configuration of main components of the endoscope system according to the third embodiment of the present disclosure. An endoscope system 1B illustrated in FIG. 7 includes an endoscope 2B instead of the endoscope 2 of the endoscope system 1 according to the first embodiment described above.

Configuration of Endoscope

The endoscope 2B illustrated in FIG. 7 includes a common-mode signal detecting unit 22B instead of the common-mode signal detecting unit 22 according to the first embodiment described above. The common-mode signal detecting unit 22B detects a reference clock signal that is a common-mode signal from an uplink signal that is transmitted in a common mode (common mode signal) from the connector 5 via the transmission cable 3 and that has the first clock edge repeated at the first frequency. The common-mode signal detecting unit 22B includes a low-pass filter circuit 222B instead of the high-pass filter circuit 222 according to the first embodiment described above. The low-pass filter circuit 222B is configured using an RC circuit including a capacitor C10B and a resistor R10B, and outputs a signal VOUT-COM_LP that is obtained by attenuating components at frequencies higher than a cutoff frequency with respect to a signal that is buffered by the buffer circuit 221.

According to the third embodiment of the present disclosure as described above, similarly to the first embodiment, it is possible to reduce the number of signal lines of the transmission cable 3 needed in the conventional technology by one, so that it is possible to reduce the diameter of the transmission cable 3.

Other Embodiments

Various embodiments may be made by appropriately combining a plurality of structural elements disclosed in the first, the second, and the third embodiments of the present disclosure described above. For example, it may be possible to remove some structural elements from all of the structural elements described in the first and the second embodiments of the present disclosure described above. Further, it may be possible to appropriately combine structural elements described in the first, the second, and the third embodiments of the present disclosure described above.

Furthermore, in the first, the second, and the third embodiments of the present disclosure, the control device and the light source device are configured as separate devices, but may be configured integrally.

Moreover, in the first, the second, and the third embodiments of the present disclosure, "a unit" described above may be replaced with "a means" or "a circuit". For example, the control unit may be replaced with a control means or a control circuit.

Furthermore, the common-mode signal transmitting unit described in the first, the second, and the third embodiments of the present disclosure is explained to transmit a simple square wave for simplicity of explanation, but may adopt a square wave that is subjected to a pre-emphasis process for increasing only (rising and falling) high-frequency components of the square wave in advance to compensate for attenuated high-frequency components in the transmission cable. The common-mode signal transmitting units 54 and 54A may include a pre-emphasis mechanism (not illustrated).

Moreover, while the endoscope system is adopted in the first and the second embodiments of the present disclosure, it is possible to adopt, for example, a capsule endoscope, a video microscope that captures an image of a subject, a mobile phone having an imaging function, or a tablet terminal having an imaging function.

While some embodiments of the present disclosure have been described in detail above based on the drawings, the embodiments are described by way of example, and the present disclosure may be embodied in various other modes with various changes and modifications based on knowledge of a person skilled in the art, in addition to the embodiments described in this specification.

According to the present disclosure, it is possible to reduce a diameter of a transmission cable.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A signal processing system comprising:
   a transmission channel including at least a pair of signal lines;
   a common-mode signal transmitting circuit configured to output an uplink signal having a first clock edge that is repeated at a first frequency to the transmission channel in a common mode;
   a common-mode signal detecting circuit configured to detect a common-mode signal from the uplink signal transmitted by the transmission channel;
   a downlink reference clock signal generating circuit configured to generate a downlink reference clock signal at a second frequency with reference to the first clock edge of the common-mode signal detected by the common-mode signal detecting circuit;
   a downlink data generating circuit configured to generate downlink data based on the first clock edge of the common-mode signal detected by the common-mode signal detecting circuit;
   a differential signal transmitting circuit configured to output, as a downlink signal, the downlink data generated by the downlink data generating circuit to the transmission channel in a differential mode, based on the downlink reference clock signal generated by the downlink reference clock signal generating circuit; and
   a differential signal receiving circuit configured to receive the downlink signal transmitted by the transmission channel and extract a differential signal from the downlink signal.

2. The signal processing system according to claim 1, wherein the second frequency is higher than the first frequency.

3. The signal processing system according to claim 1, wherein the downlink data generating circuit includes at least an imaging element that generates image data by receiving light and performing photoelectric conversion on the light, or one physical sensor that detects one or more of physical quantities of acceleration, temperature, pressure, humidity, magnetism, ion concentration, and a radiation dose.

4. The signal processing system according to claim 1, wherein
   the common-mode signal transmitting circuit is configured to output at least one of a pulse-width-modulated signal obtained by modulating a pulse width of the uplink signal and an amplitude-modulated signal obtained by modulating an amplitude of the uplink signal to the transmission channel, and
   the common-mode signal detecting circuit is configured to detect the pulse-width-modulated signal or the amplitude-modulated signal from the uplink signal transmitted from the transmission channel.

5. The signal processing system according to claim 4, wherein the pulse-width-modulated signal or the amplitude-modulated signal includes a data pattern corresponding to a horizontal synchronous signal.

6. The signal processing system according to claim 1, wherein the transmission channel further includes a power supply line and a ground line.

7. An endoscope comprising:
   the signal processing system according to claim 1;
   an insertion portion to be inserted into a subject; and
   a connector removably connected to a control device that performs predetermined image processing, wherein
   the insertion portion includes the common-mode signal detecting circuit, the downlink reference clock signal generating circuit, the downlink data generating circuit, and the differential signal transmitting circuit, and the connector includes the common-mode signal transmitting circuit and the differential signal receiving circuit.

\* \* \* \* \*